United States Patent
Mohanty et al.

(10) Patent No.: US 11,715,772 B1
(45) Date of Patent: Aug. 1, 2023

(54) FIELD-CONTROLLED SENSOR ARCHITECTURE AND RELATED METHODS

(71) Applicant: FemtoDx, Inc., Beverly Hills, CA (US)

(72) Inventors: Pritiraj Mohanty, Beverly Hills, CA (US); Shyamsunder Erramilli, Quincy, MA (US)

(73) Assignee: FemtoDx, Inc., Beverly Hills, CA (US)

( * ) Notice: Subject to any disclaimer, the term of this patent is extended or adjusted under 35 U.S.C. 154(b) by 0 days.

(21) Appl. No.: 15/691,598

(22) Filed: Aug. 30, 2017

Related U.S. Application Data

(60) Provisional application No. 62/381,143, filed on Aug. 30, 2016.

(51) Int. Cl.
| | |
|---|---|
| *H01L 29/40* | (2006.01) |
| *H01L 29/786* | (2006.01) |
| *H01L 29/06* | (2006.01) |
| *G01N 27/414* | (2006.01) |
| *G01N 33/543* | (2006.01) |
| *G01N 27/30* | (2006.01) |

(52) U.S. Cl.
CPC .......... *H01L 29/402* (2013.01); *G01N 27/30* (2013.01); *G01N 27/4145* (2013.01); *G01N 33/5438* (2013.01); *H01L 29/0673* (2013.01); *H01L 29/78648* (2013.01); *H01L 29/78696* (2013.01)

(58) Field of Classification Search
CPC ..... G01N 27/30; G01N 27/00; G01N 27/4145; G01N 33/5438; G01N 27/327; G01N 33/53; H01L 29/0673; H01L 29/402
See application file for complete search history.

(56) References Cited

U.S. PATENT DOCUMENTS

| | | | | |
|---|---|---|---|---|
| 2004/0200734 | A1* | 10/2004 | Co et al. ............ | G01N 27/4145 205/777.5 |
| 2008/0009002 | A1* | 1/2008 | Gruner et al. ......... | B82Y 15/00 435/6.11 |
| 2008/0283875 | A1* | 11/2008 | Mukasa et al. ........ | B82Y 10/00 257/253 |
| 2010/0032653 | A1* | 2/2010 | Takeda et al. ......... | B82Y 10/00 257/24 |

(Continued)

*Primary Examiner* — Brian J. Sines
(74) *Attorney, Agent, or Firm* — Wolf, Greenfield & Sacks, P.C.

(57) ABSTRACT

A nanoelectric field effect sensor uses the field created by the surface charge profile of biomolecular binding to modulate the current flowing between a source and a drain. We have shown that a patterned side or top gate can be used to calibrate the biomolecular field modulation. This approach provides an electrical sensitivity characterization of the sensor before exposing it to sample fluid. Furthermore, a side gate or a top gate voltage with the right sign can be used to control the binding event during functionalization or sensing. For instance, a negative gate voltage can prevent binding of negatively charged proteins on a sensor. This approach of electric-field control of binding can be used in a differential sensor configuration as well. For instance, in a two-sensor single-bridge technique, one of the sensors can be exposed to a local electric field to prevent binding events, which can then be used for background cancellation in a second sensor, not exposed to the electric field. Furthermore, this approach can be used to prepare a sensor chip for multiplexing, where different chip areas can be turned on or off by applying local electric fields.

7 Claims, 15 Drawing Sheets

(56) References Cited

U.S. PATENT DOCUMENTS

| | | | | |
|---|---|---|---|---|
| 2010/0152057 | A1* | 6/2010 | Lieber et al. | B82Y 30/00 506/9 |
| 2010/0216256 | A1* | 8/2010 | Cheng et al. | B82Y 15/00 436/524 |
| 2011/0159481 | A1* | 6/2011 | Liu et al. | C12Q 1/48 435/6.11 |
| 2014/0106338 | A1* | 4/2014 | Fischer | G01N 27/44791 435/5 |
| 2018/0024092 | A1* | 1/2018 | Haque | H01L 29/42364 422/69 |

* cited by examiner

FIELD-CONTROLLED SENSOR ARCHITECTURE AND RELATED METHODS

RELATED APPLICATIONS

This application claims priority to U.S. Provisional Application No. 62/381,143, filed Aug. 30, 2016, which is incorporated herein by reference in its entirety.

FIELD

The present application is related to the field of sensors used to sense chemical or biological species (also referred to as analytes), for example in an analyte solution (sample). More particularly, the present disclosure is related to nanoscale sensors, such as sensors implemented using semiconductor devices, or similar small-scale electrical devices, as sensitive transducers to convert chemical activity of interest into corresponding electrical signals representative of the chemical activity. Even more particularly, this disclosure is related to the manner in which a specific sensor within a sensor array can be activated or deactivated by the application of an electrical signal such as a bias voltage.

BACKGROUND

Silicon nanochannel field effect transistor (FET) biosensors are one of the most promising technologies in the development of highly sensitive and label-free analyte detection.

SUMMARY

Sensors used to sense chemical or biological species are described.

In one aspect, a sensor is provided. The sensor comprises a surface functionalized with a receptor configured to bind to or capture a biological or chemical entity. The sensor further comprises a gate electrode configured to apply an electric field.

In one aspect, a sensor is provided. The sensor comprises a surface functionalized with a receptor configured to bind to or capture a biological or chemical entity. The sensor further comprises a gate electrode configured to apply a first electric field a second gate electrode configured to apply a second electric field. A first signal is generated by the first electric field and a second signal iis generated by the second electric field.

In one aspect, a sensor is provided. The sensor comprises a surface functionalized with a receptor configured to bind to or capture a biological or chemical entity. The sensor further comprises a gate electrode configured to apply an electric field and an integrated circuit.

Further aspects are described below.

DESCRIPTION

Sensors used to sense chemical or biological species (also referred to as analytes) are described herein. In some embodiments, the sensors are silicon nanochannel field effect transistor (FET) biosensors. With their exceptional electrical properties and small dimensions, silicon nanochannels may be ideally suited for extraordinarily high sensitivity. In fact, the high surface-to-volume ratios of these systems make single molecule detection possible. Further, FET biosensors offer the benefits of high speed, low cost, and high yield manufacturing, without sacrificing the sensitivity typical for traditional optical methods in diagnostics. Top down manufacturing methods leverage advantages in Complementary Metal Oxide Semiconductor (CMOS) technologies, making richly multiplexed sensor arrays a reality.

Figure 1:
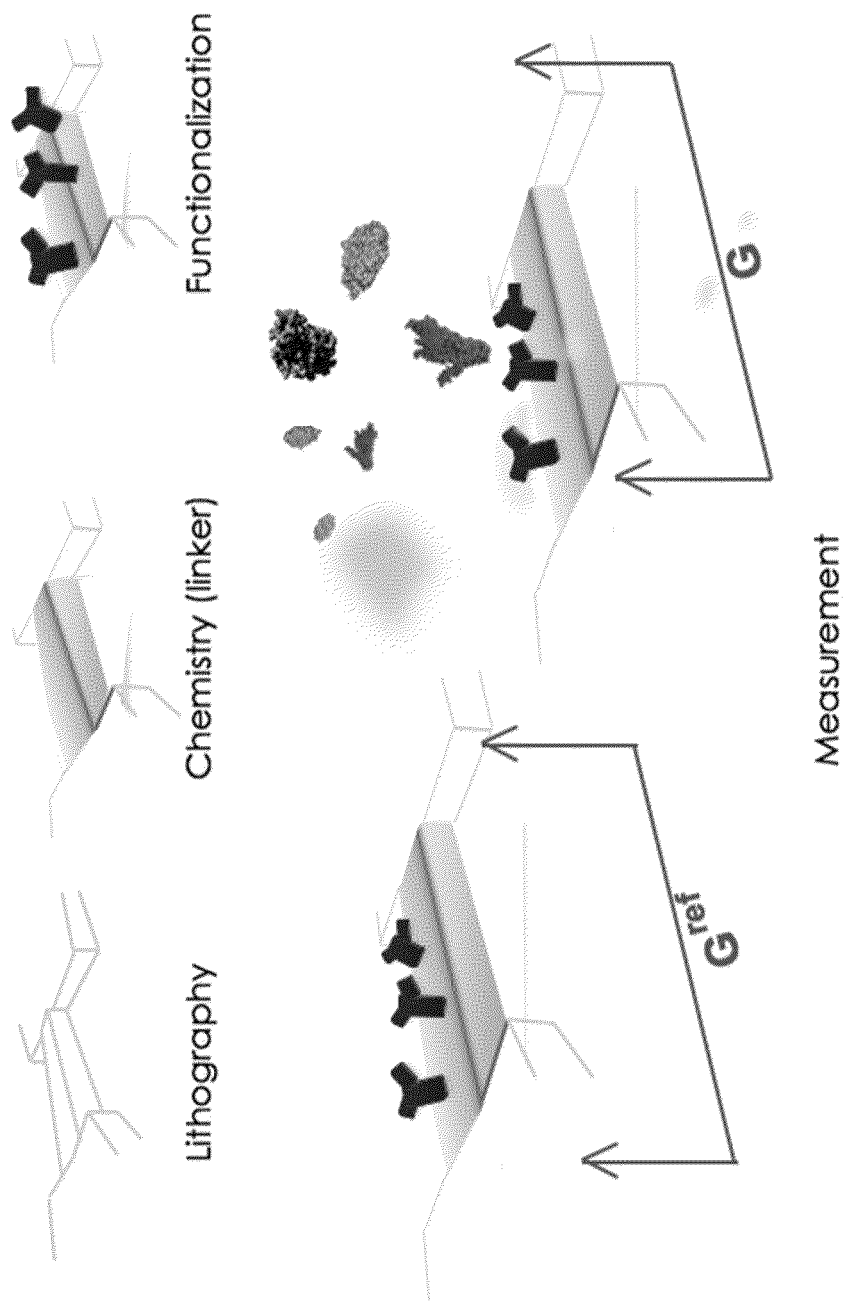
FIG. 1. The diagram indicates the stepwise manufacturing of FET devices for diagnostics tests. Nanosensors of precise dimensionality and surface area are formed that are highly sensitive to surface charge changes. Following a process of lithography and chemistry, antibodies are conjugated to the surface of the sensor (shaded area). Analyte measurements are conducted with samples containing heterogeneous mixtures of disease-relevant proteins, such as in blood, saliva, and other fluids. Specific analyte binding contributes to a surface charge differential. Detected electrically as a change in conductance (delta G, DG) across the nanosensor surface. Unshaded areas are a source and a drain for every nanosensor.

FET biosensors are adapted for the measurement of biomolecules interacting with such a sensor surface. As with other forms of sensing, the surface of a FET biosensor is modified to selectively recognize specific analytes. In the illustration shown in FIG. 1, antibodies are conjugated to the surface as part of the manufacturing process. These antibodies are selected for specific detection of a protein of interest. Molecular binding events between the analyte and the antibodies on the biosensor surface cause changes to the biosensor surface charge density and/or surface potential. In this manner, precision manufacturing of FET biosensors allows sensitive analyte recognition. The differential conductance amplitude is correlated to the analyte concentration in the sample solution.

Nanoscale Silicon-based FET devices show sensitivity, reliability, robustness and the sensor flexibility needed in multiplexed diagnostics microarrays. By developing and implementing the nanoscale devices on traditional top-down silicon, the reliability and robust quality of top-down Silicon semiconductor manufacturing processes can be improved and error rates in testing, both in point-of-care and central reference labs can be reduced. This innovation will directly result in increased effectiveness of each patient visit to a lab or clinic, reduced cost of diagnosis, and earlier diagnosis, treatment, and monitoring. Traditional detectors are not suitable for such applications.

Silicon-based nanosensor devices are also well suited as the sensing element in a wearable device, which can be used to monitor body's vitals such as blood glucose level, triglyceride level, cholesterol level and other indicators/markers, and sense disease specific analytes such as cardiac biomarkers. Because silicon is biocompatible, such sensors can be either placed on the skin as a patch or implanted in the body as an implantable sensor.

Use of Gates in Silicon Nanowire Field Effect Transistor

A field effect transistor (FET) uses an electric field to control the electrical channel of conduction, and hence the conductivity of the charge carriers in the channel. The flow of charge carriers between the source and the drain can be tuned by modifying the size and the shape of the conducting channel by applying an electric field to the gate. In the biosensor configuration, the FET consists of a nanowire channel between the source and the drain terminals. The nanowire surface can be bio-functionalized so that a biomolecular binding event can create an electric field, similar to the control electric field applied to a conventional FET. In devices that use the FET principle, a designated, physically separated sensor surface is formed by precision manufacturing. The FET sensor is connected to an electronic circuit to monitor the specific conductance of this sensor surface. Therefore, operationally, many independent electronic circuits may be interrogated in a massively parallel manner.

Gates are used to control or manipulate the current through a conducting channel. This can be used to modify or amplify the signal, as it is commonly done in transistors. Typically, a top gate is used in a MOSFET (Metal Oxide Semiconductor Field Effect Transistor) to modify the source-drain current. In other configurations, a side gate bias can be applied to achieve the same effect. In yet another configuration, a back gate bias can be applied to a metallized bottom surface of the substrate. For some applications, it is also possible to use a combination of these gates to accomplish the desired effect. These gates can be fabricated as a part of the semiconductor manufacturing process, which may include optical lithography or e-beam lithography or other methods of patterning electrodes on the surface. In certain configurations, it is possible to have a gate embedded between two layers of materials on the substrate surface.

Example: pH Detection

In one embodiment, the device is operated as a nanoelectronic pH sensor. The essential advantage of this approach is the complete control over physical and electronic degrees of freedom. The geometry and alignment of the nanowire can be fully controlled by e-beam lithography and standard semiconductor processing techniques. Furthermore, physical gate electrodes next to the nanowire can be fabricated with complete control over their location and size. These local gate electrodes enable controlled accumulation or depletion of surface charge carriers on the nanowire, and provide the ability to tune the nanowire conductance, necessary for the optimization of the detection sensitivity. In this configuration, the nanowire pH sensor regains the control and the benefits, usual in standard electronic FET devices.

Device Fabrication and Functionalization

Figure 2:
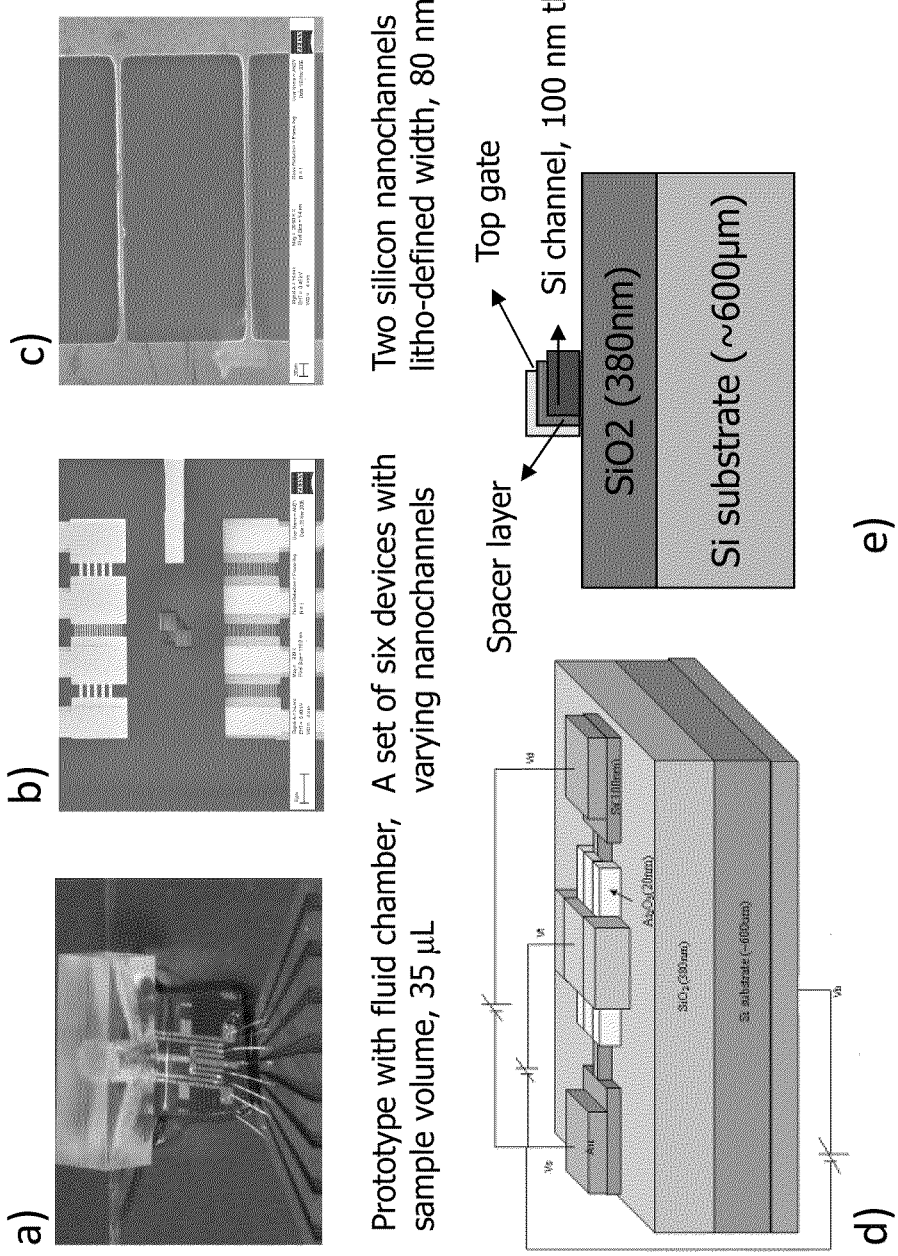
FIG. 2. a) A prototype with a fluid chamber mounted on top of the nanosensor. The fluid chamber shown here has a sample volume of 35 microliter. b) Scanning electron micrograph of a set of six devices with nanochannels with varying widths. c) Two silicon nanochannels with lithographically defined width of 80 nm. d) A schematic diagram of a single nanowire field effect transistor, containing a source and a drain, and a top gate, fabricated on top of the nanowire channel. The conduction channel can be controlled by applying an appropriate gate bias (voltage) to the top gate. e) A cross-sectional view of the silicon nanochannel, a spacer layer (typically aluminum oxide or silicon oxide), and a top gate (typically gold/titanium or gold/chromium).

The engineering of the device consists of two fundamental steps: fabrication and functionalization.
  (a) Nanofabrication: The silicon nanowire along with the side gates and the electrodes are fabricated by standard electron beam lithography and surface nanomachining. The starting SOI (Silicon on Insulator) wafer has a device layer thickness of 230 nm and oxide layer thickness of 370 nm with a starting device-layer volume resistivity of 1-2 ohm-cm. The device-layer resistivity is further controlled by doping the wafer by ion implantation of boron with a concentration of $1\times10^{18}$ /cc by ion implantation. After patterning the nanowires and the electrodes in separate steps with separate masks, the structure is etched out with an anisotropic reactive-ion etch (RIE). This process exposes the three surfaces of the silicon nanowire along the longitudinal direction as shown in the schematic diagram in FIG. 2. After the fabrication of the silicon nanowire and the gold electrodes and gates, a protective layer of polymethylmethacrylate (PMMA) is spun on the surface and only the silicon nanowire is exposed by a secondary e-beam exposure, while the device floor of oxide remains covered. This process allows exposure of only the silicon nanowire to air/solution.
  (b) Functionalization: The nanowire surface is functionalized by the application of a 2% APTES solution of methanol for 3 hours. After multiple rinsing of the device by methanol, the device is dried by nitrogen gas and baked at 80 C in an oven for 10 minutes. Following this APTES functionalization technique, the plastic flow chamber is attached to the device with the application of PMMA and silicone gel (FIG. 2(a)). The flow chamber is designed to include inlet and outlet tubes, connected to a syringe pump, to allow solution flow over the functionalized nanowire inside the chamber. The volume of the flow chamber is estimated to be ~ 35 microliter.

Measurement of Conductance and Zero-Bias Differential Conductance

Figure 3:
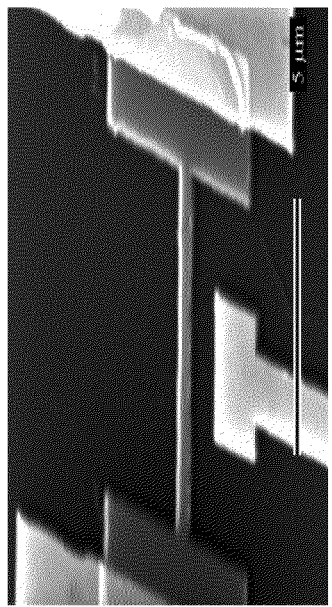
FIG. 3. (Left) A nanowire field-effect transistor functionalized for detection of bio/chemical species. The device has two gate effects; the first gate is the effect of the biomolecules bound to the nanowire surface (as shown on the right) and the control gate, fabricated on the side (as shown on the scanning electron microscope picture on the left).
Figure 3:
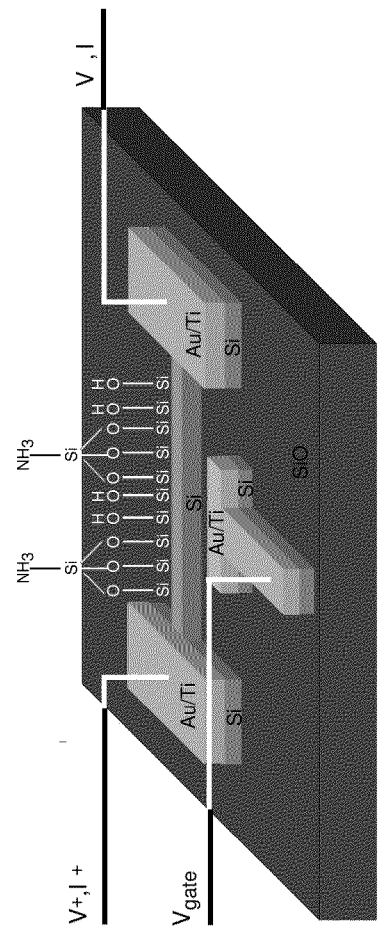

Measurement of pH-dependent conductance in presence of solution is carried out in two separate methods. The first method is the standard two-probe I-V measurement of the nanowire along with a gate voltage applied to one of the side gates shown in FIG. 3(a). Because of the high resistance of the nanowire, the I-V characteristic is measured with a Keithley 2400 source meter with a current resolution of 10 pA. Additionally, an Agilent 4339B high-impedance bridge is used to for calibration and comparison. In order to discern small changes in the pH-dependent conductance, we have used a second, more elaborate technique of differential conductance (dI/dV) measurement. The measurement circuit includes a small AC modulation (provided by an EG&G 5210 lockin amplifier), superimposed on the DC bias across the nanowire (provided by the Keithley 2400 source meter). The AC modulation and the DC bias are added by a noninverting summing circuit, which is integrated with the preamplifier circuit. The circuit is then put in a RF-shielded aluminum box to prevent noise pickup. Differential conductance measurements are done by sweeping the DC bias at a constant AC modulation amplitude, and measuring the response with the lockin amplifier, referenced to the AC signal frequency.

FIG. 4(a) shows a typical I-V characteristic of a silicon nanowire in air; the nanowire is 300 nm wide, 230 nm thick and 10 mm long, doped with a boron concentration of $1\times10^{18}$ /cc. FIG. 4(b) displays the differential conductance (dI/dV) of the same nanowire. As clearly elucidated in FIG. 4(b), the nanowire conductance is not ohmic; otherwise the differential conductance would have been independent of the bias, contrary to what is shown in FIG. 4(b). Our approach allows the measurement of zero-bias conductance, avoiding bias-dependent effects in the solution such as electrolysis.

Figure 5:
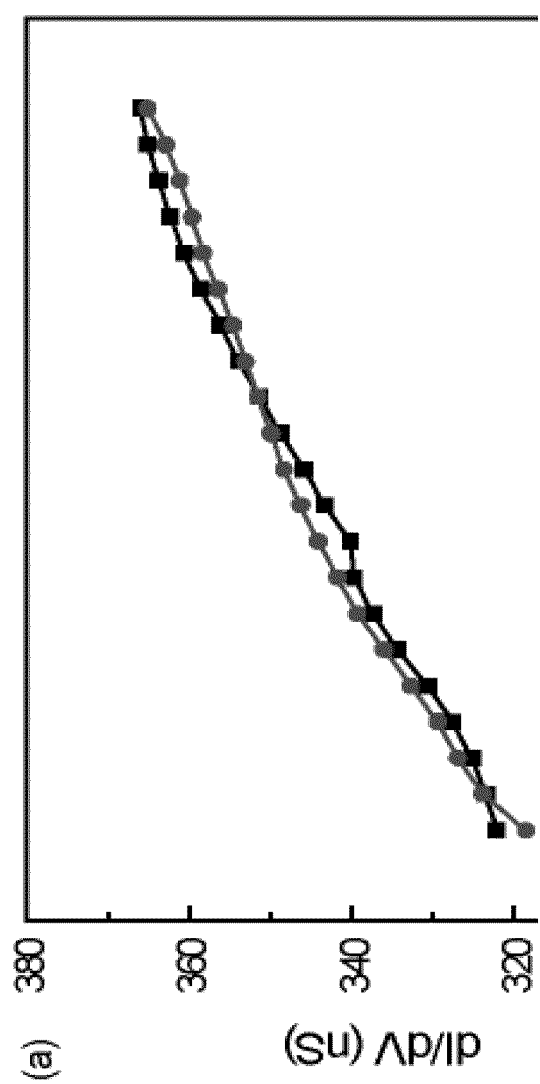
FIG. 5. Zero-bias differential conductance (dI/dV) with increasing (a) and decreasing (b) pH values of the solution. (c) dI/dV for the two sets of measurements shown in (a) and (b). (d) dI/dV for an arbitrary sequence of pH values demonstrates reproducibility. The measurements are done with an AC drive at 37 Hz with an amplitude of 50 mV.

FIG. 5 displays zero-bias differential conductance of the functionalized nanowire in pH solution. Solutions with varying hydrogen ion concentration or pH are made from PBS (phosphate buffered saline), containing 10 mM of phosphate and 130 mM of salt. The zero-bias conductance of the nanowire increases with increasing pH, consistent with previous measurements. FIGS. 5(a) and 5(b) show zero-bias conductance change with the increasing and decreasing sequence in pH change; FIG. 5(d) shows a random sequence of pH change with the corresponding change in zero-bias conductance.

Figure 6:
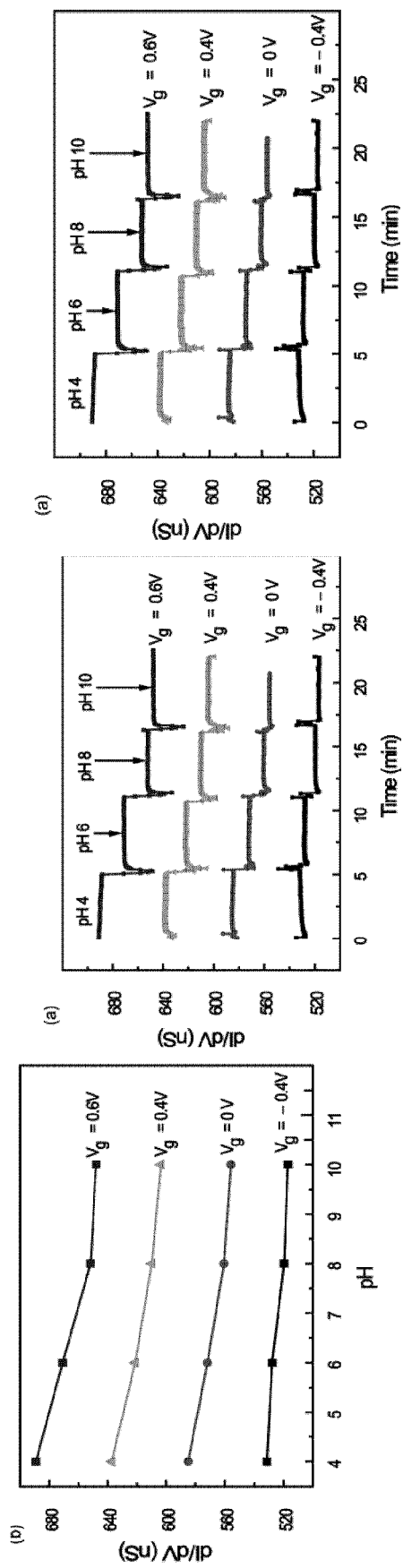
FIG. 6. (a) Zero-bias differential conductance (dI/dV) with increasing pH values of the solution at different gate voltage. (b) dI/dV versus pH value of the solution at different gate voltage. (c) Difference in dI/dV at pH 4 and pH 10 at different gate voltage. The data points for Vg = 0.6 V were shifted by 40 nS for clarity in FIG. 4(a) and FIG. 4(b).

Further evidence of field effect is demonstrated by zero-bias conductance measurement at different gate voltage, shown in FIG. 5. The zero-bias conductance is tuned by the application of the side-gate voltage. A positive gate bias implies opening of the charge carrier channel, similar to the inversion layers in silicon devices. A negative gate bias implies depletion or squeezing of the charge carrier channel, similar to depletion layer. The zero-bias conductance increases or decreases depending on positive or negative gate bias, respectively. In FIG. 6(a) and FIG. 6(b), the data points for Vg = 0.6 V were shifted by 40 nS for clarification. As FIG. 6(c) demonstrates, not only the absolute conductance but also the difference in dI/dV at two pH values of the solution increases with increasing gate voltage.

Detection Sensitivity for pH Sensing

The pH detection sensitivity of our fully engineered silicon nanowire sensor is determined to be 5 nS/pH. Further enhancement of sensitivity of our sensors can be done by reducing the dimensions of the silicon nanowire to increase the effective surface-to-volume ratio; reducing the doping concentration of the starting SOI wafer for optimized conductance; creating a better ohmic contact between the electrodes and the underlying silicon surface by local doping; and optimizing the flow-chamber design for faster throughput.

To summarize, fabrication, functionalization and operation of a nanoelectronic field-effect pH sensor are demonstrated. The physically engineered silicon nanowire with side gates is fabricated with standard semiconductor processing techniques. The functionalized silicon nanowire can be controlled with local nanoscale side gates to induce inversion or depletion layers. Our approach offers the possibility of highly parallel detection of ion or charged protein and DNA with local control of individual elements. By selectively gating, individual nanowires in an array can be turned on or off during functionalization. Therefore the array can contain multiple receptors for the simultaneous detection of multiple chemical and biological species in a single integrated chip.

Figure 7:
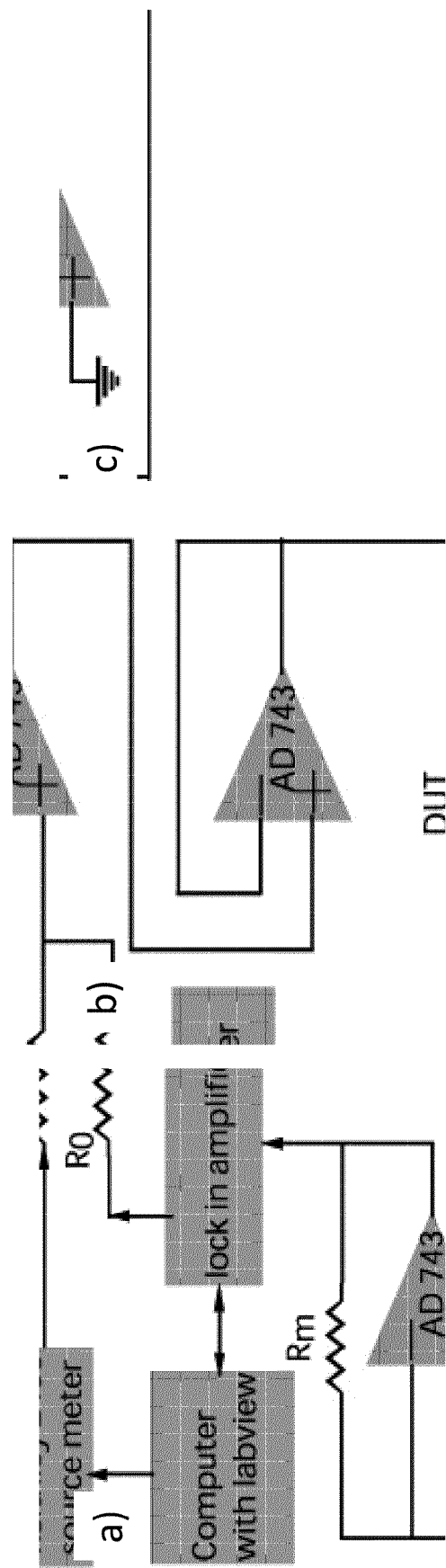
FIG. 7: Device schematic diagram and scanning electron micrographs. The schematic diagram of the silicon nanowire with side gates and electrodes. The nanowire is exposed on three sides along the longitudinal directions. (a) The nanowire shown here is 300 nm wide, 230 nm thick and 8 µm long. (b) A silicon nanowire with an Au/Ti side gate. An appropriate bias (voltage) can be applied to the side gate to prevent functionalization (c) The scanning electron micrograph displays three silicon nanowire devices on the same chip. In this example, the three nanowires can be selectively functionalized, so that the difference between the signals from a functionalized nanowire device and a non-functionalized nanowire device can be used to determine the actual signal amplitude corresponding to the concentration of the analyte in the fluid sample.

Of particular interest in the location of a control gate in the devices in FIG. 7(b) and FIG. 7(c). This gate, shown in 7(b), has allowed to enhance the sensitivity and to control the labeling of the nanowire leading to a new method of using nanosensors for biomarkers. Without any gate biasing, one can measure the presence of the model marker at a concentration of less than 1 ng/ml. By adjusting the gate voltage, the sensitivity is increased by at least 1 order of magnitude. The estimated sample volume sensed is about 1 femtoliter. More interestingly, the effect of pH can be mimicked by changing the gate voltage, increasing sensitivity and control by electrically "tuning" the electric field near the nanosensor past the pK value of a selected biomarker target group. This ability of using gate voltage to increase sensitivity is shown in 7(c). Increasing the gate voltage increases the differential conductance change as the ion concentration is changed. Conversely, the gate voltage can be used to "tune" the effective local ion concentration near the nanosensor, using a Field-Effect principle. This suggests that a suitable gate voltage can be used effectively to change "local pH" in a few femtoliters of solvent that are near the nanosensor. By changing the local proton ion concentration past the nominal chosen pK value, it is possible to control simply by using gate voltages the ability of a biomarker to bind or not, thus allowing for selective coating of the nanowire with specific antibodies or peptides or other analytes.

A Model of Nanoscale Field Effect Transistor and the Effect of Gates

A comprehensive model of charge transport to analyze conductance signal as well as amplification characteristics for calibration of the biomolecular concentration shows the dependence observed for pH detection and other biomarker detection. Detection of cancer antigens is also performed following the same approach.

There are two gate effects arising from the device design. The first, and the essential, gate effect arises because cancer antigen biomolecules bind to the layer of antibody on the surface, changing the dielectric constant of the antibody layer. This acts as a (biological) gate, which modulates the conduction channel in the nanowire. The second gate, physically fabricated on the side is designed to provide control over the conduction channel. By applying a side gate voltage (positive or negative), the dielectric effect of the biomolecules can be enhanced. The enhancement or amplification effect has been shown earlier.

Figure 4:
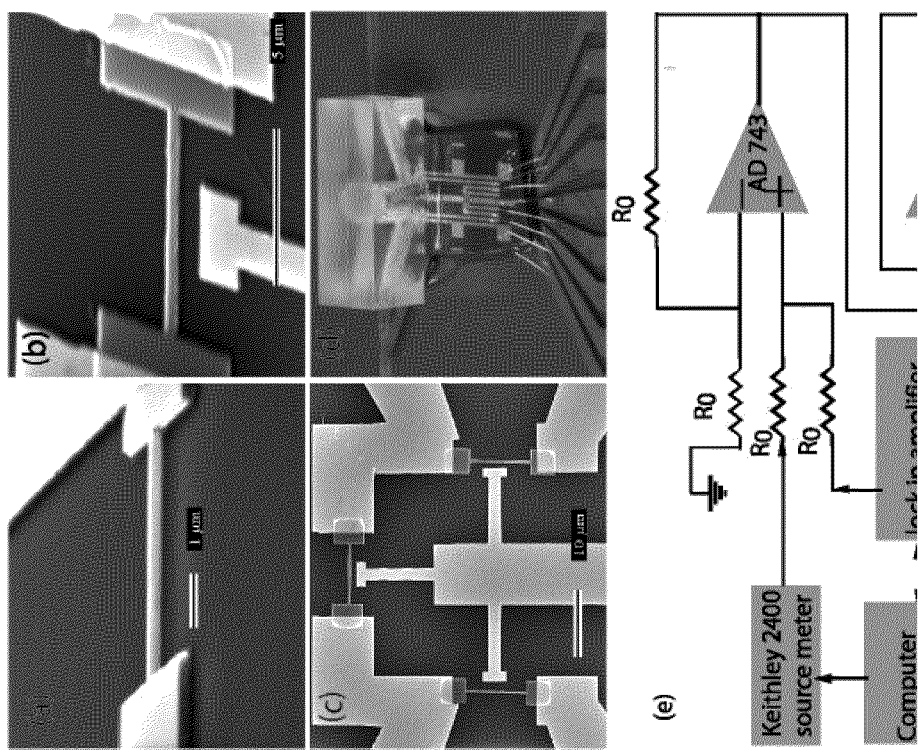
FIG. 4. A typical I-V characteristic of a doped silicon nanowire device. (b) A typical differential conductance dI/dV characteristic of the same nanowire shows nonohmic behavior. In this measurement, an AC signal at 10 Hz with amplitude of 50 mV is used.
Figure 8:
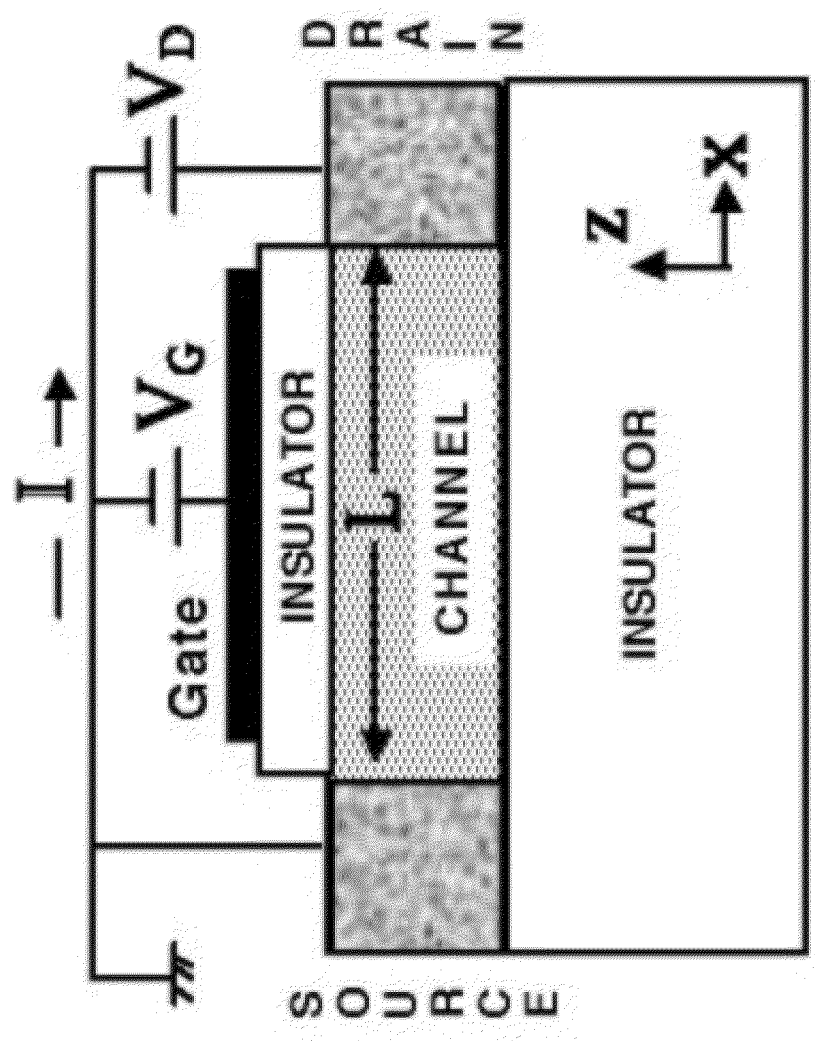
FIG. 8. A schematic diagram of a field effect transistor with top gates. The conduction characteristics depend on the channel dimensions as well as the proximity of the gate.

The device is modeled as a FET where the gate potential Vg is provided by biomolecular binding on the surface. The simplest model of the device is shown in FIG. 8. It consists of a semiconducting narrow channel, which allows current to flow from source to drain, and the two contact pads are assumed to be highly conducting. The voltage on the gate controls the electron density in the channel. If the channel potential is halfway between the source and drain potential then there will be current flow for both forward and reverse bias in a symmetric way. However, if the gate potential is tied to the source potential, then the I-V characteristic will look similar to a rectifier and the asymmetry in the I-V curve can be used to estimate the energy gap. The slight asymmetry in FIG. 4 shows that device geometry and parameters can be controlled to a high degree to realize a specific energy level in the conduction channel.

Figure 9:
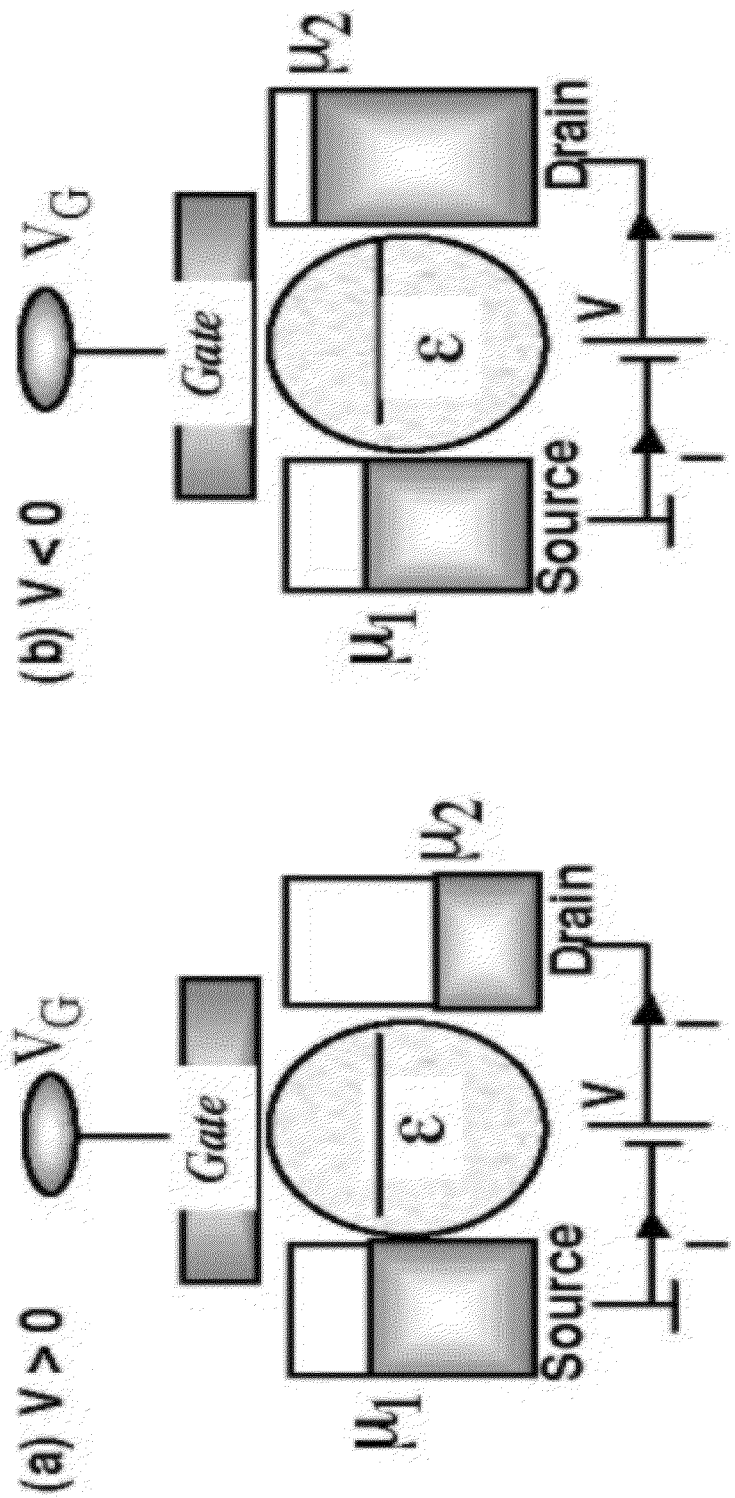
FIG. 9. The schematics (a and b) show potential profile for net positive or negative gate voltage. Depending on whether the channel potential is tied to the source and not the drain, the device can behave as a rectifier, enabling current flow in the forward bias. Modeling of the potential profile enables the appropriate characterization of the nanowire biosensor device.

The device can function in the n-type or p-type transistor configuration depending on the gate effect (FIG. 9), which is the net effect arising of biomolecular binding and the control gate voltage. If the net gate voltage is positive, then the energy levels in the conduction channel of the nanowire will be lowered. Since the energy levels in the source and the drain are unchanged (due to large contact area between the contact pads and the silicon surface), the electrochemical potential delta has to remain unchanged. Therefore the energy levels E move with respect to the electrochemical potential, driving the latter into empty bands. This makes the transistor more conductive and turns it ON, as the current flow in the channel depends on the number of energy levels available around $E = \mu$. Likewise, a net negative voltage will result in a p-type operation. In order to define transistor characteristics with respect to biomolecular interaction, electron flow through the nanowire channel needs to be modeled. The model is a modified version of standard transistor model, which takes into account the nanoscale dimensions of the nanowire. Since the cross-sectional dimensions of the nanowire determine the number of energy levels, the dependence of the transistor parameters such as conductance and zero-bias differential conductance will depend on the transistor dimensions as well as the dielectric characteristics of the antibody-antigen layer.

Since the channel is an insulator with a very high resistance in the high-megaohm range, the potential profile is calculated by solving the Laplace equation with appropriate boundary conditions. The potential energy of the channel is defined in terms of the electronic charge, source-drain voltage and gate voltage and the capacitances between the channel (nanowire) and the source, drain and gate, respectively. In addition to analytical models, numerical solution of the Laplace equation with inputs provided by the experimental devices can also be helpful in characterizing the device behavior.

Other Gate Configurations

Figure 10:
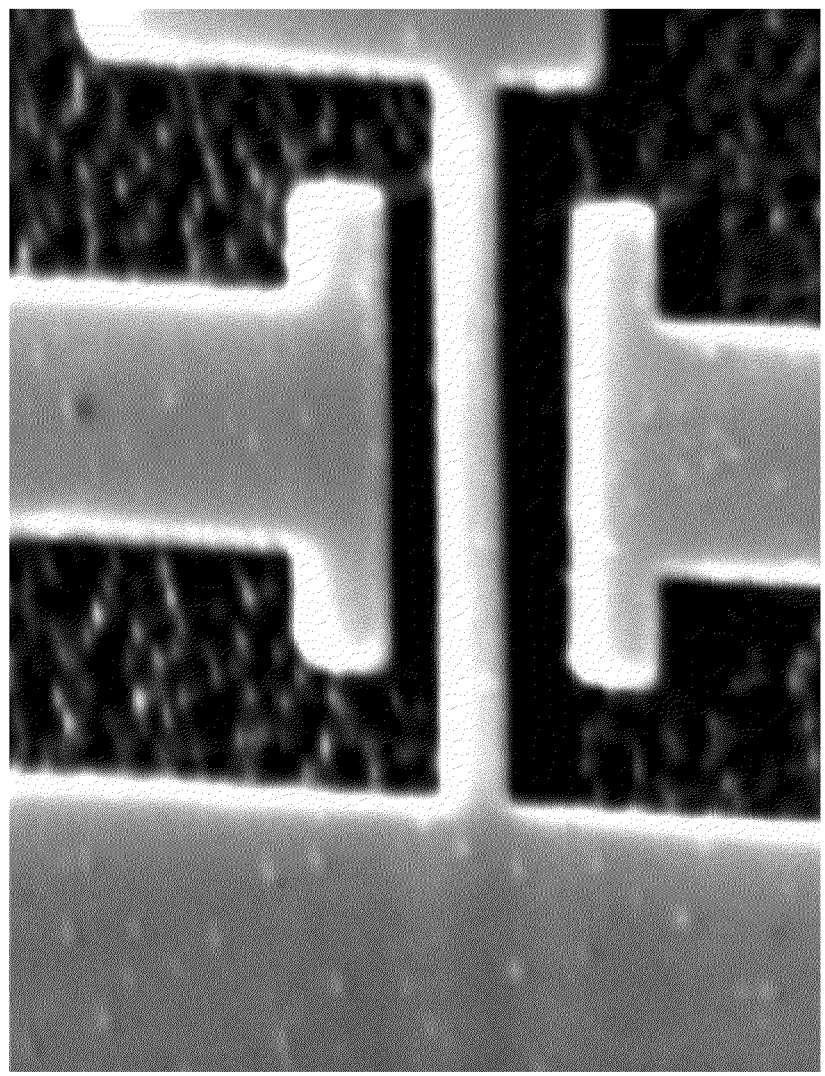
FIG. 10. A silicon nanowire with two side gates, designed to provide additional control to the conductance change in the central nanowire due to biomolecular binding.
Figure 11:
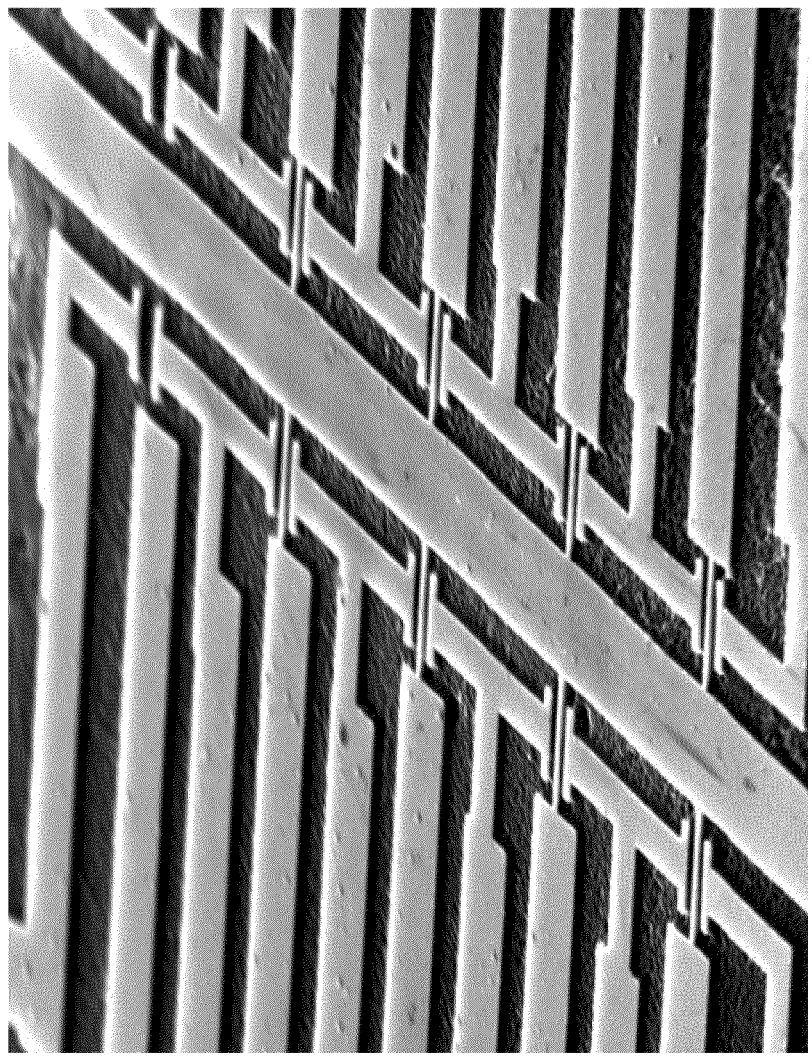
FIG. 11. A series of silicon nanowire devices can be used for differential configuration for higher sensitivity or in an array configuration for detecting multiple species.

FIG. 10 demonstrates a nanowire with two side gates, which can be used to apply two gate voltages to discern the effect of biomolecular binding, which also has the effect of a separare gate. Both gates can be employed for selective functionalization or for the calibration of the binding effect in terms of a gate voltage. FIG. 11 shows an array of such nanowire sensors with two side gates.

Figure 12:
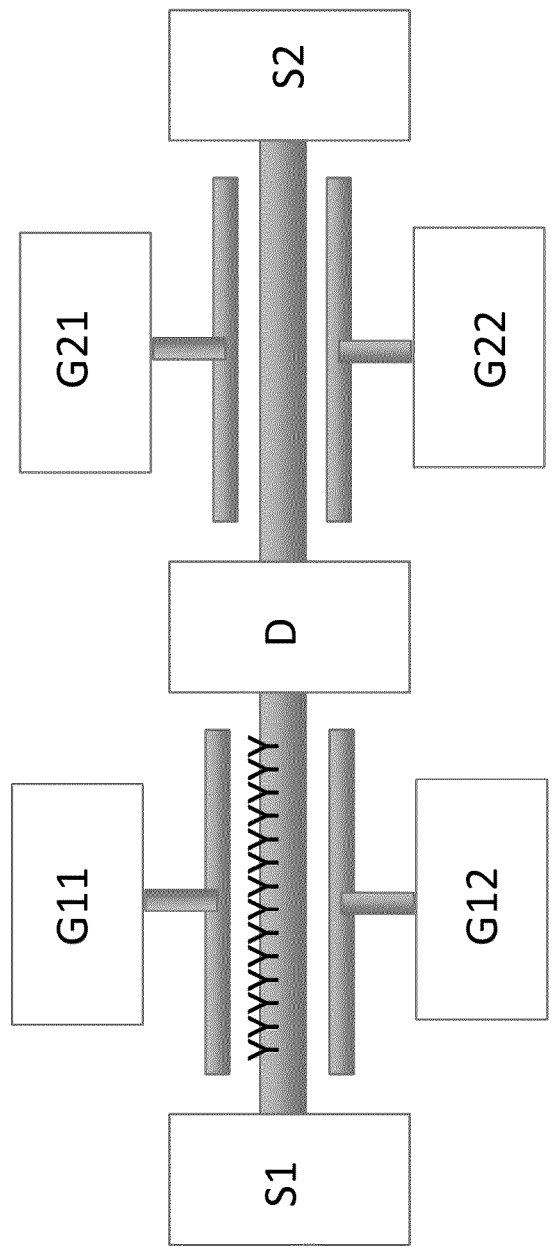
FIG. 12. A device containing two nanowire field effect transistors. The first nanowire transistor contains a source (S1) and a drain (D), and side (or top) gates (G11 and G12). The second nanowire transistor contains a source (S2) and a drain (D) and two gates (G21 and G22). Either G21 or G22 or both can be used during the functionalization process to prevent the second nanowire from being functionalized, while the first nanowire is being functionalized.

FIG. 12 shows a configuration in which two sensors are used. In this configuration, background can be subtracted by functionalizing one nanowire sensor (contained between S1 and D) and not functionalizing the second nanowire sensor (contained between D and S2). The functionalization process can be prevented for the second nanowire by applying suitable gate voltages to the gates G21 and/or G22, as shown in the figure. Similarly, top gates (that are patterned on the wire), back gates (that are patterned on the back side of the wafer) or floating gates (that are electrodes in the fluid) can be used for similar purpose.

Figure 13:
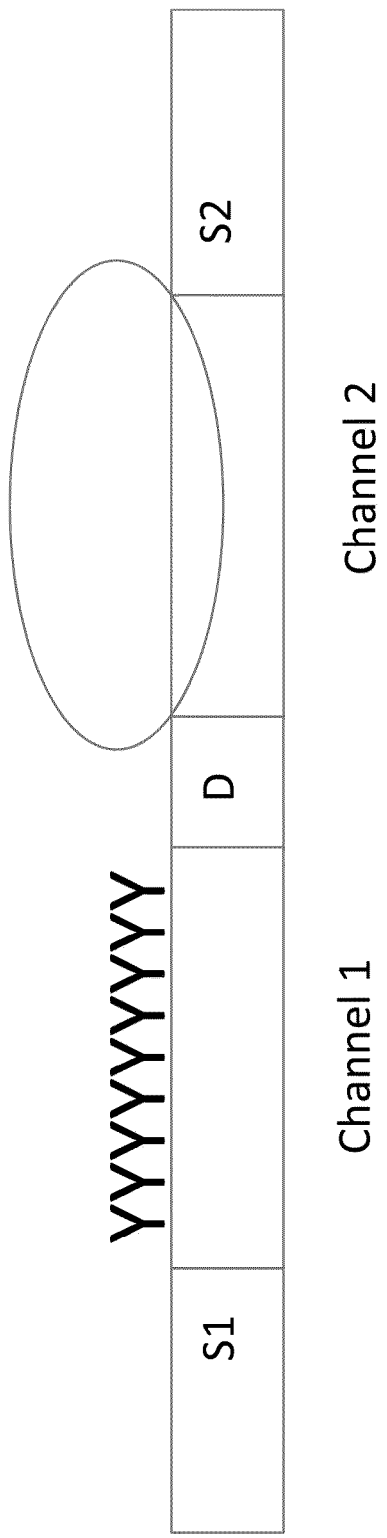
FIG. 13. Side view of a device containing two nanowire field effect transistors. The first nanowire transistor contains a source (S1) and a drain (D), and the second nanowire transistor contains a source (S2) and a drain (D). A gate bias can be used on the second nanowire during the functionalization process to prevent the second nanowire from being functionalized, while the first nanowire is being functionalized. This is achieved by creating an electrical shield around the second nanowire by applying the appropriate bias to the gate (or gates).

FIG. 13 shows a side view, where one of the two sensors can be selectively functionalized. The difference between the signals arising from the two sensors therefore will provide a better background subtraction, and hence an accurate determination of the presence of the analyte and its concentration in the fluid sample. The concept described here for two sensors can be easily extended to a sensor network containing more than two sensors.

Figure 14:
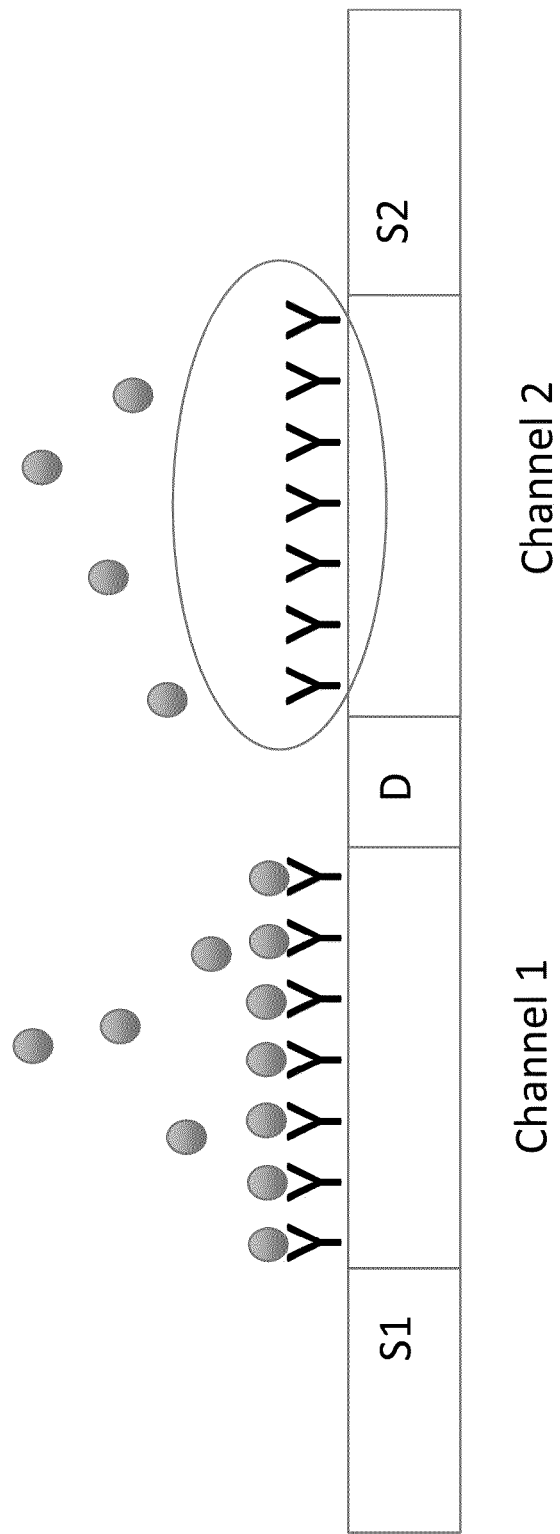
FIG. 14. Side view of a device containing two nanowire field effect transistors. The first nanowire transistor contains a source (S1) and a drain (D), and the second nanowire transistor contains a source (S2) and a drain (D). A gate bias can be used on the second nanowire during the functionalization process to prevent the second nanowire from being functionalized, while the first nanowire is being functionalized. This is achieved by creating an electrical shield around the second nanowire by applying the appropriate bias to the gate (or gates).

FIG. 14 shows a different two sensor configuration where both sensors are equally functionalized. However, during measurement, it is possible to apply an appropriate gate voltage to one of the sensors (the second one in the figure) to create the appropriate electrostatic screening effect so that the particular sensor (the second one in the figure) will not come in contact with the analyte to be detected. The difference between the signals arising from the two sensors will provide a better determination of the presence of the analyte and its concentration. This concept can be extended to a configuration containing more than two sensors. In addition, a network of sensors can be designed for multiplexed sensing where gates can be employed to selectively tune in or out a given sensor during the measurement of a particular analyte, and the approach can be repeated for a second sensor corresponding to a second analyte and so on.

Figure 15:
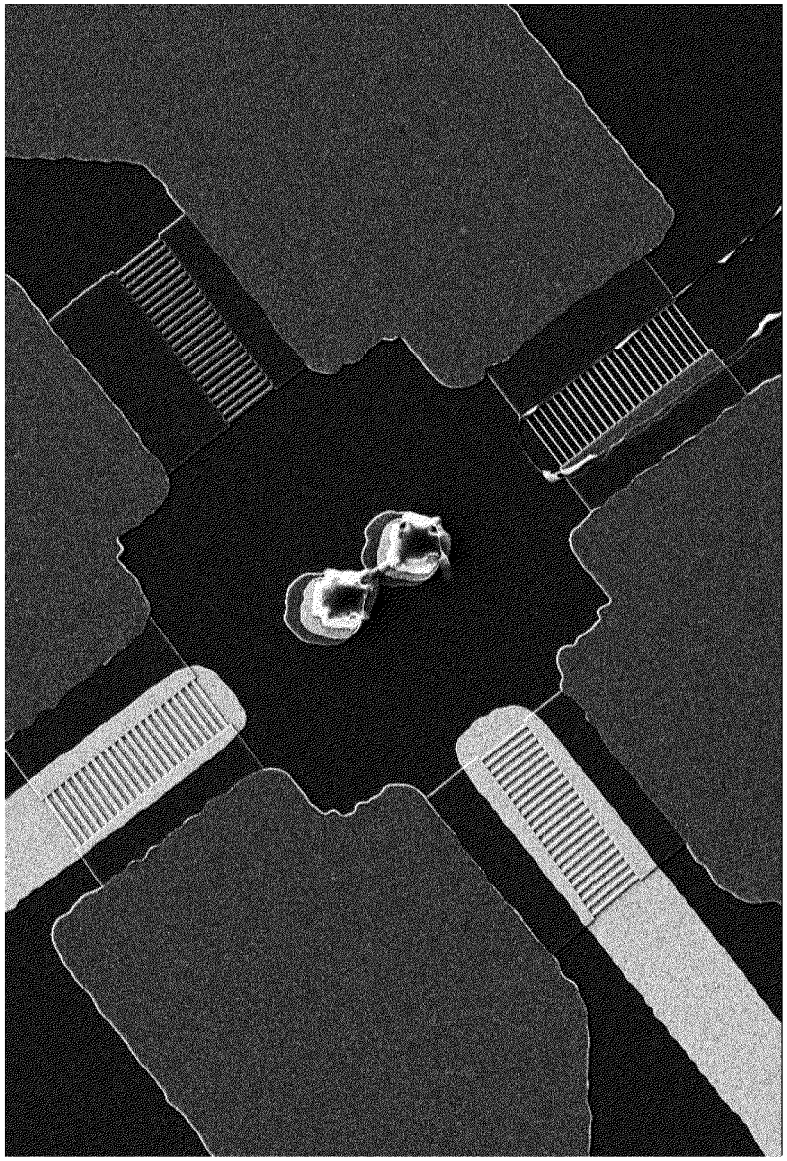
FIG. 15. A four-sensor device in a Wheatstone bridge setup. The lower left and top electrodes are top gate electrodes and are used to adjust the resistance of the wires to allow for balanced bridge operation or for selective functionalization.

FIG. 15 shows a four-sensor device where two of the sensors have top electrodes used for selective functionalization or for tuning the resistance of the underlying sensors.

The invention claimed is:

1. A sensor comprising:
a substrate;
a silicon nanowire formed on the substrate, the silicon nanowire including a surface functionalized with a receptor comprising an antibody configured to bind to or capture a biological or chemical entity;
a first gate electrode configured to apply a first electric field to the silicon nanowire, wherein the first gate electrode is located on a top of the silicon nanowire; and
a second gate electrode configured to apply a second electric field to the silicon nanowire, wherein the second gate electrode is located on the substrate on a side of the silicon nanowire.

2. A sensor as decribed in claim 1, where the first gate electrode is configured to apply the first electric field to control functionalization of the surface of the silicon nanowire.

3. A sensor as described in claim 1, where the first gate electrode is configured to apply the first electric field to prevent binding of the receptor to selected areas on the surface of the silicon nanowire.

4. A sensor as described in claim 1, where the first gate electrode is configured to apply the first electric field to prevent binding of the receptor to selected areas on the surface of the silicon nanowire to define a baseline signal representing absence of the biological or chemical entity.

5. A sensor as described in claim 1, where first gate electrode is configured to apply the first electric field using the first gate electrode during the process of binding of the biological or chemical entity to the receptor on the surface of the silicon nanowire.

6. A sensor as described in claim 1, where the first gate electrode is configured to apply the first gate voltage at a magnitude determined by the charge on the biological or chemical entity to be detected by the sensor.

7. A sensor as described in claim 1, where first gate electrode and the second gate electrode are configured to apply a sequence of the first gate voltage and the second gate voltage to control binding of the biological or chemical entity to selected areas on the surface of the silicon nanowire.

* * * * *